United States Patent [19]

Pocius

[11] 4,295,932
[45] Oct. 20, 1981

[54] SYNERGISTIC BLEND OF BIOCIDES

[75] Inventor: Frances C. Pocius, Westmont, Ill.

[73] Assignee: Naloc Chemical Company, Oak Brook, Ill.

[21] Appl. No.: 168,858

[22] Filed: Jul. 14, 1980

[51] Int. Cl.³ .............................................. D21H 5/22
[52] U.S. Cl. ..................................... 162/161; 162/190; 210/764
[58] Field of Search ................ 162/161, 190; 210/764

[56] References Cited

U.S. PATENT DOCUMENTS 3,236,726  2/1966  Ross .................................... 210/764
3,523,121  8/1970  Lewis et al. ......................... 424/270
3,929,561  12/1975 Shema et al. ....................... 162/161

Primary Examiner—William F. Smith
Attorney, Agent, or Firm—John G. Premo; Robert A. Miller

[57] ABSTRACT

A method for controlling the microorganism in aqueous systems comprising treating such systems with a biocidal amount of a mixture of 75% of 5-chloro-2-methyl-4-isothiazolin-3-one and 25% 2-methyl-4-isothiazolin-3-one with chlorine or chlorine dioxide.

5 Claims, No Drawings 4,295,932

SYNERGISTIC BLEND OF BIOCIDES

INTRODUCTION

The formation of slime by microorganisms is a problem which attends many systems. For example, lagoons, lakes, ponds, pools, and such systems as cooling water systems and pulp and paper mill systems all possess conditions which are conductive to the growth and reproduction of slime-forming microorganisms. In both once-through and recirculating cooling systems, for example, which employ large quantities of water as a cooling medium, the formation of slime by microorganisms is an extensive and constant problem.

Airborne organisms are readily entrained in the water from cooling towers and find this warm medium an ideal environment for growth and multiplication. Aerobic and heliotropic organisms flourish on the tower proper while other organisms colonize and grow in such areas as the tower sump and the piping and passages of the cooling system. Such slime serves to deteriorate the tower structure in the case of wooden towers. In addition, the deposition of slime on metal surfaces promotes corrosion. Furthermore, slime carried through the cooling system plugs and fouls lines, valves, strainers, etc. and deposits on heat exchange surfaces. In the latter case, the impedance of heat transfer can greatly reduce the efficiency of the cooling system.

In pulp and paper mill systems, slime formed by microorganisms is also frequently and, in fact, commonly encountered. Fouling or plugging by slime also occurs in the case of pulp and paper mill systems. Of greater significance, the slime becomes entrained in the paper produced to cause breakouts on the paper machines with consequent work stoppages and the loss of production time or unsightly blemishes in the final product which result in rejects and wasted output. The previously discussed problems have resulted in the extensive utilization of biocides in cooling water and pulp and paper mill systems. Materials which have enjoyed widespread use in such applications include chlorine, organo-mercurials, chlorinated phenols, organo-bromines, and various organo-sulfur compounds. All of these compounds are generally useful for this purpose but each is attended by a variety of impediments. For example, chlorination is limited both by its specific toxicity for slime-forming organisms at economic levels and by the ability of chlorine to react which results in the expenditure of the chlorine before its full biocidal function may be achieved. Other biocides are attended by odor problems and hazards in respect to storage, use or handling which limit their utility. To date, no one compound or type of compound has achieved a clearly established predominance in respect to the applications discussed. Likewise, lagoons, ponds, lakes, and even pools, either used for pleasure purposes or used for industrial purposes for the disposal and storage of industrial wastes, become, during the warm weather, beseiged by slime due to micoorganism growth and reproduction. In the case of the recreation areas, the problem of infection, etc. is obvious. In the case of industrial storage or disposal of industrial materials, the microorganisms cause additional problems which must be eliminated prior to the materials use or the waste is treated for disposal.

Naturally, economy is a major consideration in respect to all of these biocides. Such economic considerations attach to both the cost of the biocide and the expense of its application. The cost performance index of any biocide is derived from the basic cost of the material, its effectiveness per unit of weight, the duration of its biocidal or biostatic effect in the system treated, and the ease and frequency of its addition to the system treated. To date, none of the commercially available biocides have exhibited a prolonged biocidal effect. Instead, their effectiveness is rapidly reduced as the result of exposure to physical conditions such as temperature, association with ingredients contained by the system toward which they exhibit an affinity or substantivity, etc., with a resultant restriction or elimination of their biocidal effectiveness.

As a consequence, the use of such biocides involves their continuous or frequent addition to systems to be treated and their addition to a plurality of points or zones in the systems to be treated. Accordingly, the cost of the biocide and the labor cost of such means of applying it are considerable. In other instances, the difficulty of access to the zone in which slime formation is experienced precludes the effective use of a biocide. For example, in a particular system there is no access to an area at which slime formation occurs and it may only be applied at a point which is upstream in the flow system. However, the physical or chemical conditions, e.g., chemical reactivity, thermal degradation, etc. which exist between the point at which the biocide may be added to the system and the point at which its biocidal effect is desired render the effective use of a biocide impossible.

Similarly, in a system experiencing relatively slow flow, such as a paper mill, if a biocide is added at the beginning of the system, its biocidal effect may be completely dissipated before it has reached all of the points at which this effect is desired or required. As a consequence, the biocide must be added at a plurality of points, and even then a graduated biocidal effect will be experienced between one point of addition to the system and the next point downstream at which the biocides may be added. In addition to the increased cost of utilizing and maintaining plural feed points, gross in economies in respect to the cost of the biocide are experienced. Specifically, at each point of addition, an excess of the biocide is added to the system in order to compensate for that portion of the biocide which will be expended in reacting with other constituents present in the system or experience physical changes which impair its biocidal activity.

It is now known that the mixture of 75% 5-chloro-2-methyl-4-isothiazolin-3-one and 25% 2-methyl-4-isothiazolin-3-one which is sold under tradename of Kathon-886 by Rohm and Haas may be blended with certain sulfones to produce a synergistic biocide. This is the subject matter of U.S. Pat. No. 3,929,561.

Kathon-886 is effective at low dosages, e.g. a few parts per million, for treating industrial systems contaminated with a wide variety of microorganisms. These microorganisms include bacteria, molds, fungi, yeast and algae. In many cases, however, in order to achieve good control of microbiological growth in industrial cooling systems, Kathon-886 must be used at high dosages, e.g. in excess of 10 ppm. When such badly contaminated systems are treated with Kathon-886, it is relatively impossible to reduce the total count to a low level. Due to the high cost of Kathon-886, it is, therefore, not practical to use this material for controlling aqueous industrial systems which are heavily contaminated by microorganisms. Such systems containing heavy microorganism contamination are the type of system which benefit most from the practice of the instant invention.

These heavily contaminated systems are often further characterized as containing large amounts of deposits which are composed of dead microorganism masses. In severe cases they can often have the appearance of bearded slimes.

THE INVENTION

A method for controlling heavy microorganism contamination in aqueous systems comprises treating such systems with a biocidal amount of a mixture of 75% of 5-chloro-2-methyl-4-isothiazolin-3-one and 25% 2-methyl-4-isothiazolin-3-one with chlorine or chlorine dioxide.

Chlorine and Chlorine Dioxide

Chlorination practices used to treat industrial cooling waters very considerably. Most often, the chlorine or chlorine-releasing compound is slug-fed or maintained at a low dosage in the system and then allowed to act on the microorganisms present in the system. As the chlorine acts on the microorganisms and is in contact with organic matter often present in such systems, it is absorbed or chemically reacted to the point that it is no longer detectable as free chlorine. Thus, the systems are treated to provide so-called chlorine residuals which, in most cases, rarely exceed 2-3 ppm and, in most cases, rarely exceed 1 ppm. A typical chlorine residual that would occur from typical chlorination practices would be about 0.2 ppm.

In addition to chlorine, chlorine dioxide is used to a somewhat lesser extent in treating industrial processed water such as cooling water and paper mills. It also may be slug fed or maintained at a low dosage.

Chlorine or chlorine dioxide, when used at the dosages mentioned above, are incapable of controlling to any great degree systems which are heavily contaminated with microorganisms. In such systems, common doses of chlorine are incapable of giving any substantial reduction to the high counts found in such systems.

For purposes of further defining the invention, systems that are heavily contaminated with microorganisms is meant to include those systems having recirculating water total counts greater than 1 million and which are incapable of experiencing substantial count reduction when treated separately with low dosages of either chlorine or Kathon-886.

One of the most surprising features of the invention is that when the Kathon-886 is used in conjunction with the chlorine, it is possible, in many instances, to reduce the total count to 0 and in some instances maintain it at this level.

In a preferred practice of the invention, it is beneficial to use a so-called biodispersant as an adjunct to the Kathon-886 and chlorine treatment thus described. By biodispersant is meant a surface active agent capable of dispersing existing biomass deposits of the type found on surfaces in industrial water systems, thereby rendering the microorganisms from such deposits into a suspended finely divided state and therefore susceptible to attack by biologically active chemicals.

It is now known that not all surface active agents work with equal effectiveness as biomass dispersants. Frequently, tests must be run to determine the efficacy of such materials to disperse deposits composed predominantly of microorganisms. In the practice of the invention, it has been found that a good class of biodispersants are propylene oxide-ethylene oxide block copolymers, which polymers comprise a polyoxy-propylene glycol polymer having a molecular weight of from 1500-2000 which has been reacted with from 5-30% by weight of ethylene oxide. In a preferred embodiment of the invention, these polymers are employed at a dosage rate varying between 0.5-50 ppm and, most preferably, 0.5-30 ppm.

Specific examples of such polymers are polyoxypropylene glycol base molecule which has a molecular weight of about 1750. In one case, this polyoxypropylene glycol base is reacted with 10% by weight of ethylene oxide and has an average molecular weight of about 2000. This is referred to as Dispersant A hereafter. Another similar dispersant is the same polyoxypropylene glycol base reacted with 20% by weight of ethylene oxide. It has an average molecular weight of about 2500.

While the above represents a preferred group of biodispersants for use in the practice of the invention, other nonionic polymers may be used, typical of which would be a $C_{18}$ fatty alcohol reacted with from about 6-12 moles of ethylene oxide. While cationic dispersants may be used, they are not too desirable since they tend to produce heavy foam.

The amount of Kathon-886 used in conjunction with the chlorine or chlorine dioxide is in the range of 0.5-10 ppm with an optimum dosage being 0.5-2 ppm. When the Kathon-886 is used alone at this dosage, it is incapable of substantially reducing the count in heavily microorganism-contaminated systems. Similarly, the amount of chlorine or chlorine dioxide used in the practice of the invention will be an amount of incapable of controlling such systems when used alone.

The ratios between the Kathon-886 and the chlorine and chlorine dioxide may be varied broadly and still good biological control of cooling tower systems will be achieved.

ILLUSTRATION OF THE INVENTION

EXAMPLE 1

An industrial plant having a cooling system containing 500,000 gallons of water and a severe biological fouling problem was treated with shock chlorination and a separation treatment which included shock chlorination plus the addition of the active compounds which are the subject of this application. Prior to the start of the program, the microbiological analysis of the waters contained within this industrial system indicated that the organism count per milliliter was in excess of 1 million. Two hours of shock chlorination treatment which left a chlorine residual immediately following the treatment in excess of 1 ppm, treated the water in such a way as to achieve an organism count per milliliter of NEG. 1/1000 (this indicates that 1 ml. of the cooling tower water diluted to 1000 milliliters gave no active biological growth on an appropriate biological testing plate containing nutrients.)

However, within 24 hours following this shock chlorination, the microbiological organism count again exceeded 1 million organisms per ml.

The next day a 1 hour shock chlorination occurred simultaneously with treatment of the water with approximately 1 ppm of the active materials previously described. Immediately following this treatment, a sample of the cooling water again demonstrated a NEG. 1/1000 organism count. This time, however, prolonged biological monitoring indicated a NEG. 1/1000 biological organism count for the next 48 continuous hours. It is obvious from these results that a profound synergistic result is obtained with the use of chlorine and the active compounds, 5-chloro-2-methyl-4-isothiazolin-3-one and 2-methyl-4-isothiazolin-3-one.

Approximately 60 hours later, a sample taken from the industrial recirculating cooling water system again showed microbiological counts in excess of 1 million. At this time the system was again shocked with a two hour treatment of chlorine. Shortly after this two hour shock chlorination, the microbiological count dropped to a NEG. 1/1000 result. However, within 9 hours, the organism count exceeded 10,000, and within 24 hours, the organism count exceeded 10 million. This recycled test, that is, two hour shock chlorination followed by monitoring of the results obtained; a 1 hour shock chlorination with the addition of approximately 1 ppm of the active ingredients of the present invention, followed again by microbiological organism monitoring, and finally a repeat of the 2 hour shock chlorination treatment without the addition of the active compounds, indicates the benefit derived by the use of the active compounds of the instant invention simultaneously with chlorine to achieve a synergistic result and vastly improve microbiological controls.

Continued testing at this same industrial site continued to demonstrate that the combination of shock chlorination with the active microbiocides of this invention provided vastly improved microbiological control within this industrial cooling water system. Simple chlorination using a typical shock treatment did not achieve the desired results and this type of shock treatment was only acceptable in combination with the use of at least 1 ppm of the active ingredients of the instant invention.

EXAMPLE 2

The same industrial cooling water system, containing approximately 500,000 gallons of recirculating cooling water, used in the test outlined in example 1, was treated for five days with the compounds of the instant application and with no shock chlorination whatsoever. On the second and fourth days of this five day monitoring period approximately 0.9 ppm of the active ingredients of this invention were added in a "shock" or slug treatment procedure. The microbiological monitoring demonstrated that the organism count per milliliter dropped below 1 million on only one occasion during this monitoring period.

However, the microbiological organism counts never exceeded more than 1.5 million and following the slug treatment of our active component, a log decade drop in microbiological activity was observed.

In spite of the log decade decrease in organism count per milliliter, a good result was not obtained when using the active compound of this invention as the *only* treatment for this system. The system required the simultaneous treatment of chlorine and the active components previously described as adequate microbiological controls for this system using this type of shock treatment.

Continued monitoring of this system for the next two weeks indicated that shock chlorination gave inadequate microbiological control unless at least 1 ppm of the active compounds previously described was also maintained in the recirculating cooling water system.

EXAMPLE 3

At a second industrial site in the southwest part of the country, an extended program was carried out to demonstrate the use of chlorine, the use of the previously described microbilogical dispersants, and the use of the active compounds of the instant invention.

This industrial site had been receiving microbiological treatment which included the addition of approximately 20 ppm of a second microbiocide referred to as 2,2-dibromonitriloproprionamide (20%). This microbiological treatment was being added at 20 ppm dosages on Mondays, Wednesdays, and Fridays of each week while the system was being treated continuously with from 200 to 300 lbs. of chlorine per day. The system had a capacity of approximately 500,000 gallons with an open tower deck and was in a fouled condition prior to the addition of the compounds of the instant invention. Even considering the fact that a microbiocide, dibromonitrilopropionamide, was being added along with continuous chlorination, the tower condition was such that the microbiological monitoring indicated a fouled condition and the on-site microbiological plate counts averaged approximately 45,000 organisms per milliliter of recirculating cooling tower. This data was accumulated on site and accounts for the much lower numbers than the data previously reported in examples 1 and 2 which were sampled on site, sent through the mail (following time for continued microbio growth) subsequently leading to higher counts than will be reported for this test.

For approximately two weeks prior to the beginning of the test program using the combination of the ingredients of the instant invention, the cooling water system described in this example gave a microbiological organism count per ml. of approximately 45,000 with a maximum count reaching approximately 130,000 and a low count of approximately 11,000. This averaged 44,790 microorganisms per milliliter. Starting on Oct. 1, 1979, about 3 ppm of a microbiological dispersant[1] of this invention was added at a dose of about 3 ppm active compound in the water system. Samples were immediately taken after the addition of the dispersant and sent to the laboratory in Chicago. After this sample had been taken, approximately 0.9 ppm of the active microbiocide was added. Throughout this test chlorine was being added at a rate equivalent to 300 lbs. per day.
[1]Dispersant A The initial test sample was taken in the presence of the microbiological dispersant and the residual chlorine which was achieved through the 300 lb. chlorination controlled addition program. This sample, when analyzed later in the Chicago Laboratory, indicated a microorganism count per milliliter approaching 1 million.

Shortly after the microbiological dispersant was added and the 0.9 ppm microbiocide was added another sample was taken for microbiological organism analysis. This sample indicated a NEG. 1/1000 microorganism count per milliliter as did the samples taken for the next 72 hours. A program which included the addition of the microbiological dispersant at a slug treatment of 3 ppm based on the total water in the recirculating system and the addition of 0.9 ppm of the microbiological biocide (same basis) of the instant invention was added to the system on Mondays, Wednesdays, and Fridays of each week. The monitoring of this system indicated that no microbiological activity was observed in the samples obtained during the first fourteen days of this type of treatment.

The only time samples taken from the system showed any microbiological count was when the sample was taken immediately after the addition of the microbiological dispersant and before the addition of the microbiocide of this invention.

Approximately one month into this test, the chlorine that was being added to this system was turned off. The chlorine was off for seven days during which time the microbiocide and the microbiological dispersant were continued in the manner previously described. During this period of time the microbiolgical count taken on site increased from 0 on the first day that the chlorine was turned off to 67,200 four days later, and finally to a total count of approximately 460,000 seven days after the chlorine had been turned off. (These counts were taken on site).

Eleven days after the chlorine had been turned off, it was again added at a rate between 200 and 300 lbs. per day. The initial sample taken after the addition of chlorine indicated an immediate drop in the microbiological organism count from the previously mentioned 460,000 figure to 72,300, followed during the next sampling period of a microbiological count of approximately 10,000, followed during the next biological sampling period of a biological count of slightly over 5,000, followed thereafter by two consecutive monitoring samples which showed no 0 microbiological counts, indicating return of complete control of the system.

At that time the addition of chlorine was dropped from an average of 280 lbs. per day down to an average of 125 lbs. per day while continuing the addition of approximately 1 ppm active microbiocide and approximately 3 ppm active microbiological dispersant every three days. During this period of time the on site microbiological count averaged 750, a vast improvement over the previously seen high of 464,000. For the next three weeks, the chlorine added to the system varied between 100 lbs. per day and 125 lbs. per day while the addition of microbiocide was between 0.5 ppm and 1.0 ppm and the addition of microbiological dispersant was approximately 3 ppm on a total system basis while being slug fed every other day or on the Mondays, Wednesdays, and Fridays schedule.

During this period of time the on site microbiological count averaged slightly less than 7,000 with a high of 28,000 which followed a 48 hr. period in which no chlorine was added, and a low of 0 which occurred during the test period after the chlorine had been added at a rate of 125 lbs. per day for a period of 72 hrs.

Close observance of this data indicates that the addition of the microbiocides of the instant application along with continuous chlorine treatment while in the presence of a microbiological dispersant, can achieve excellent control of a cooling water system which was previously fouled with heavy microbiological growth.

In an attempt to demonstrate that the basic synergism of the invention is that between residual chlorine and the substituted isothiazolin-3-one microbiocides, this identical industrial system was placed back on the treatment which had existed prior to the 2½ month test program just outlined. This system was augmented by the addition of 3 ppm, based on the total system, of the microbiological dispersant used during the trial outlined above.

During this period of time approximately 14–15 ppm of the 2,2'-dibromonitrilopropionamide (20%) microbiocide previously used before the trail was added to the system along with continuous addition of 200 lbs. of chlorine per day while the system was being treated every two to three days with a slug feed of approximately 3 ppm of the previously described microbiological dispersant.

Monitoring of these results indicate an average on site microbiological count of approximately 35,000. The highest microbiological count noticed during this test period were approximately 50,500 and the lowest microbiological count observed during this test period was approximately 15,500. All of these numbers were taken on site and compared quite favorably with the initial results which averaged 45,000 using this same similar treatment, but without the dispersant.

Comparison of these results clearly indicates that a synergistic result is obtained with the continuous addition of chlorine, even at reduced rates, and the microbiocides of the invention. The addition of at least 0.5 ppm of the active substituted isothiazolin-3-one microbiocides while continuously adding chlorine and the simultaneous addition of a microbiological dispersant also adds to the ability of this synergistic treatment to clean up the total system by dispersing microbiological growth which has accumulated on surfaces within the system into the recirculating water where they are immediately killed by the microbiocide combination of the instant application.

EXAMPLE 4

A third industrial site was chosen for additional testing of the efficiency of the microbiocide combination of this invention. This third industrial site maintained a cooling water system that had two towers of varying capacity operating in parallel with the incoming make up water system. One tower was maintained using the identical microbiological control treatment system which this industrial site had been used continuously for some period of time. This tower was the "control" tower.

During the test, one tower received the treatment that this plant had been using which included the addition of chlorine dioxide to the make up water for both towers. To the second tower both the microbiological dispersant[1] as well as the microbiocide of the instant invention was also added on a slug treatment basis. The microbiological dispersant was added at a level ranging from 5 ppm down to 2 ppm (based on system contents). The microbiocide active compound was added at a level of from approximately 0.5 ppm, based on the entire system treated, to a level of about 10 ppm. During a period of approximately 2 months, both towers, operating in parallel, were closely monitored for biological growth. The chlorine dioxide level was maintained at a constant rate throughout all of the tests to be reviewed. The microbiological organism counts were run on samples collected on site, properly packaged for protection, and shipped to a laboratory in Chicago for biological analysis. Tower A will be the control tower which receives only chlorine dioxide treatment at the normal level for this industrial site. Tower B will have received not only the chlorine dioxide treatment identical to that of Tower A, but also treatment with both the microbiological dispersant and the microbiocide of this instant invention. The test period was approximately two months long and the microbiological control achieved in the tower receiving additional microbiocide treatment and microbiological dispersant treatment will clearly demonstrate the efficacy of the instant invention.

¹Dispersant A

The microorganisms counts on Tower A averaged in excess of 1 million for the entire two month test period. For a one week period of time, all the chlorine dioxide feed to the make up of both of these test towers was shut off. During that period of time the microbiological monitoring demonstrated that tower A again, averaged a microbiological count exceeding 1 million and on occasion approaching 10 million organisms per milliliter of recirculating water.

Tower B, on the other hand, was treated on the first day of the monitoring period with 2 ppm of the microbiological dispersant previously described and approximately 5.5 ppm of the active biocide. The sample taken within 8 hours of this treatment indicated a microorganism count of NEG. 1/1000 or essentially no living microorganisms within the recirculating water system. This result was duplicated the next day without additional microbiocide or dispersant being added. On the third day an additional 2 ppm of microbiological dispersant was added to the system followed by the addition of approximately 3 ppm of the microbiocide. A sample taken that day again indicated essentially no microorganism growth observable in the recirculating water system. This result continued for the next four consecutive days after which time an additional 2 ppm of the microbiological dispersant and approximately 3 ppm of microbiocide was again added to the system. After this addition, continued NEG. 1/1000 results were obtained for the microbiological organism counts.

Emphasis is again placed on the fact that throughout this monitoring period Tower A was showing a microbiological count in excess of 1 million.

Several days later 5 ppm of the microbiological dispersant was added to the system. The off-site microbiological counts increased to approximately 100,000 following the addition of the microbiological dispersant. After that sample was taken and packaged for analysis approximately 1.5 ppm of the microbiocide was added to the system and continued monitoring was done on the microorganism growth in this system. The average microbiological count for the next 10 to 15 days of monitoring was well below 150,000 regardless of the addition of continued slugs of 5 ppm of the microbiological dispersant.

As the microbiological dispersant was added, samples taken indicated increased microorganism counts in the recirculating water indicating that the microbiological dispersant was effectively removing microorganisms from the surfaces of the recirculating cooling water system and placing those organisms within the recirculating water so that they could be effectively killed by the combined biocide treatment, which in this case was the synergistic use of the chlorine dioxide along with the microbiocides of the substituted isothiazolin-3-ones.

Approximately 15 days after the continued treatment of this system with the microbiodispersant and microbiocides of the instant invention, the treatment of this system with the microbiological dispersant or the microbiocides was stopped, while ClO₂ remained at the same level. The system was monitored for a period of 72 hours during which time the microorganism count increased from approximately 0 to slightly over 160,000.

At this point 0.75 ppm of microbiocides was added following the addition of about 5 ppm of the microbiological dispersant. The next sample taken indicated that there was no living microbiological organisms remaining in the circulating water system. This result essentially continued for the next several days.

Shortly after these results were obtained all chlorine dioxide was cut off to both of the towers. Tower A's microbiological growth counts again exceeded 1 million for the 7 day period in which the chlorine dioxide was not being added to the water make up of these two tower systems.

During this period of time 5 ppm of the microbiological dispersant was added to tower B 48 hrs. after the chlorine dioxide was turned off and, again, 72 hours after that. Shortly after addition of dispersant approximately 0.75 ppm of the active microbiocide was also added to tower B. Microbiological monitoring of tower B indicated that the average microbiological organism counts exceeded 1 million during this 7 day monitoring period even though two of the 7 days the tower's system received microbiological dispersant and microbiocide. The chlorine dioxide feed was again continued and microorganism monitoring of both towers also continued.

For the next three weeks the microbiological monitoring of Tower A again indicated an organism count exceeding 1 million on the average. The microbiological count of Tower B was always below 1 million and was predominantly below 10 thousand with a majority of the data indicating no microorganism count. During this three week period of time the microbiological dispersant was slug fed six separate times followed immediately by a slug feed of the microbiocide of the instant application at a concentration level of between 0.5 and 1.5 ppm, based on the entire system.

Again this test clearly indicates the synergistic effect of the active microbiocides, the substituted isothiazolin-3-one, commonly referred to as Kathon-886, with chlorine dioxide. The addition of the microbiological dispersant assists in the clean up of the total system in that it disperses microbiological growth accumulated on surfaces of the system into the recirculating water of the system where the synergistic microbiocidal effects described in this application can be best observed.

Having described the results obtained in testing of various industrial systems in the Midwest and the Southwest parts of the United States, using chlorine, chlorine dioxide, different methods of applications of these known microbiocides, along with the synergistic use of the microbiocides of the instant application and the micro dispersant described herein, I claim:

1. A method for controlling aqueous systems heavily contaminated with microorganisms comprising treating such systems with 0.5–10 ppm of a mixture of 75% of 5-chloro-2-methyl-4-isothiazolin-3-one and 25% 2-methyl-4-isothiazolin-3-one and an effective amount of chlorine or chlorine dioxide, such amount being substantially effective with said mixture to control microorganisms in the aqueous system.

2. The method of claim 1 where chlorine is used.

3. The method of claim 1 where chlorine dioxide is used.

4. The method of claim 1 where there is also present with such mixture 0.5–50 ppm of a biodispersant.

5. The method of claim 1 where the biodispersant is a propylene oxide-ethylene oxide block copolymer, which polymer comprises polyoxypropylene glycol polymer having a molecular weight of from 1500–200 which has been reacted with from 5–50% by weight of ethylene oxide.

* * * * *

UNITED STATES PATENT OFFICE
CERTIFICATE OF CORRECTION

Patent No. 4,295,932　　　　　　　Dated OCTOBER 20, 1981

Inventor(s) FRANCES C. POCIUS

It is certified that error appears in the above-identified patent and that said Letters Patent are hereby corrected as shown below:

Line 65 of Claim 5.

" polymer having a molecular weight of from [1500-200]"

should read

-- polymer having a molecular weight of from 1500-2000 --.

ON THE TITLE PAGE:
"Assignee: [Naloc] Chemical Company, Oak Brook, Ill."

should read

-- Assignee: Nalco Chemical Company, Oak Brook, Ill. --.

Signed and Sealed this

Nineteenth Day of January 1982

[SEAL]

Attest:

GERALD J. MOSSINGHOFF

Attesting Officer　　Commissioner of Patents and Trademarks